United States Patent [19]

Schuster

[11] 4,067,229

[45] Jan. 10, 1978

[54] VISCOMETER FOR INDICATING RHEOLOGICAL PROPERTIES OF BIOLOGICAL FLUIDS

[75] Inventor: Samuel R. Schuster, Wellesley, Mass.

[73] Assignee: Ovutime, Inc., Brookline, Mass.

[21] Appl. No.: 722,166

[22] Filed: Sept. 10, 1976

Related U.S. Application Data

[63] Continuation-in-part of Ser. No. 472,611, May 23, 1974, abandoned, and Ser. No. 523,047, Nov. 12, 1974, Pat. No. 3,982,423, which is a continuation-in-part of Ser. No. 462,298, April 19, 1974, abandoned, which is a continuation-in-part of Ser. No. 433,767, Jan. 16, 1974, abandoned, which is a continuation-in-part of Ser. No. 300,187, Oct. 24, 1972, abandoned.

[51] Int. Cl.² .............................................. G01N 11/00
[52] U.S. Cl. ........................................................ 73/54
[58] Field of Search ............................ 73/54, 64.4, 53; 128/2 W; 23/230 B

[56] References Cited

U.S. PATENT DOCUMENTS

| 3,926,037 | 12/1975 | Kopito et al. | 73/53 |
| 3,979,945 | 9/1976 | Kopito et al. | 73/54 |
| 3,982,423 | 9/1976 | Schuster | 73/54 |
| 4,002,056 | 1/1977 | Kopito et al. | 73/64.4 |

Primary Examiner—Richard C. Queisser
Assistant Examiner—Joseph W. Roskos
Attorney, Agent, or Firm—Morse, Altman, Oates & Bello

[57] ABSTRACT

A biological fluid is introduced into the sheer region between a pair of bearing members which are biased for relative motion and which are characterized by a particular surface finish. The rheological properties of the biological fluid are a function of the lubricity of this biological fluid.

2 Claims, 2 Drawing Figures

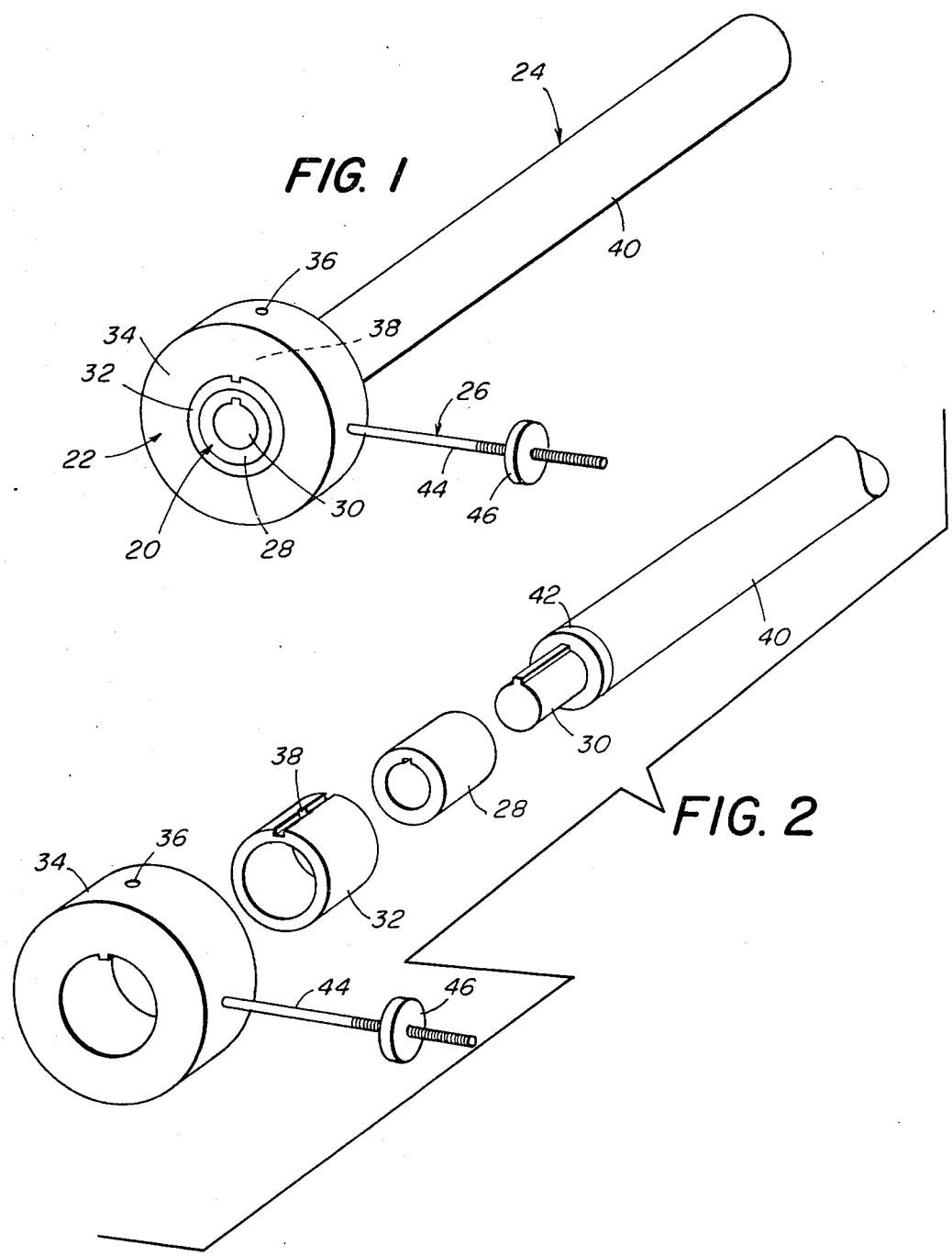

VISCOMETER FOR INDICATING RHEOLOGICAL PROPERTIES OF BIOLOGICAL FLUIDS

RELATED APPLICATIONS

The present application is a continuation-in-part of application Ser. No. 523,047, filed Nov. 12, 1974, now U.S. Pat. No. 3,982,423, issued Sept. 28, 1976, which in turn is a continuation-in-part of application Ser. No. 462,298, filed Apr. 19, 1974abandoned, which in turn is a continuation-in-part of application Ser. No. 433,767, filed Jan. 16, 1974 abandoned, which in turn is a continuation-in-part of application Ser. No. 300,187, filed Oct. 24, 1972 abandoned. The present application also is a continuation-in-part of earlier application Ser. No. 472,611, filed May 23, 1974 abandoned which in turn is a continuation-in-part of aforesaid application Ser. No. 300,187, filed Oct. 24, 1972 abandoned. The present invention also is related to application Ser. No. 629,700, filed Nov. 7, 1975 now U.S. Pat. No. 4,013,066, issued Mar. 22, 1977, which is a continuation of aforesaid application Ser. No. 472,611, filed May 23, 1974 abandoned.

BACKGROUND OF THE INVENTION

1. Field of the Invention

The present invention relates to processes and devices for determining the rheological properties of biological fluids and, more particularly, to the estimation of differential rheological properties of heterogeneous biological fluids such as saliva, ejaculates, cervical mucus and blood. Such fluids usually are composed of several liquid fractions of different chemical compositions, molecular weights and rheological properties.

2. The Prior Art

The determination of rheological properties of such heterogeneous biological fluids has been difficult because: (1) random structural variations from sample to sample complicate efforts to obtain reproducible values; (2) collection and testing of a sample can cause significant changes in its visco-elastic structure; (3) conditions in the test instrument are different from conditions in-vivo or in-situ; (4) particular measurements do not necessarily indicate particular visco-elastic structures; and (5) comparative standards of known visco-elastic structures generally are lacking. In particular, present on-the-spot testing techniques are inadequate.

SUMMARY OF THE INVENTION

The primary object of the present invention is to provide processes and devices, for testing biological fluids having high and low viscosity components, characterized by disposing a sample of such a biological fluid between a pair of bearing members which are biased for relative motion and which are characterized by surfaces of particular finish. The biological fluid establishes a lubricity, which is indicated by the relative motion between the bearing members. The rheological properties of this fluid are a function of this lubricity. In one embodiment, one of the bearing members is provided with a port through which a predetermined amount of sample fluid can be introduced in to the shear region between the bearing surfaces under standardized conditions. The present invention takes advantage of the fact that, from a clinical (rather than a purely scientific) standpoint, it frequently is not necessary to measure exact rheological values of some biological fluids in order to yield medically significant information.

Other objects of the present invention in part will be obvious and in part will appear hereinafter.

The invention accordingly comprises the products and processes, together with their parts, steps and interrelationships, which are exemplified in the present disclosure, the scope of which will be indicated in the appended claims.

BRIEF DESCRIPTION OF THE DRAWINGS

For a fuller understanding of the nature and scope of the present invention, reference is made to the following detailed specification, which is to be taken in connection with the accompanying drawings wherein:

FIG. 1 is a perpsective view of a product embodying the present invention; and

FIG. 2 is a perspective, exploded view of the components of the product of FIG. 1.

DETAILED DESCRIPTION OF THE PREFERRED EMBODIMENT

The illustrated embodiment of the present invention, as shown in FIGS. 1 and 2, comprises an inner bearing assemblage 20 and an outer bearing assemblage 22, between which a biological specimen is tested in accordance with the present invention; a support assemblage 24 for carrying inner bearing assemblage 22; and a bias assemblage 26 for causing or not causing relative motion between the inner and outer bearing assemblages during testing of a biological fluid therebetween.

As shown, inner bearing assemblage 20 includes an inner bearing ring 28 having an outer cylindrical bearing surface, which has a finish in accordance with the present invention. Bearing ring 28 has an inner cylindrical surface with a keyway. Bearing assemblage 22 also includes a cylindrical mount 30 that has an outer cylindrical surface with a key. Ring 28 and mount 30 snugly mate with each other so that they can be fitted together manually, retained in mated condition frictionally, or separated from each other manually as desired.

As shown, outer bearing assemblage 22 includes an outer bearing ring 32 having an inner bearing surface which has a finish in accordance with the present invention. Bearing ring 32 has an outer cylindrical surface with a keyway. Bearing assemblage 22 also includes an annular mount 34 that has an inner cylindrical surface with a key. Ring 32 and mount 34 mate with each other so that they can be fitted together manually, retained in mated condition frictionally, or separated from each other manually as desired.

Bearing mount 34 has a port 36 extending from its outer to its inner surface and bearing ring 32 has a port 38 extending from its outer to its inner surface. When bearing mount 34 and bearing ring 32 are mated, ports 36 and 38 are aligned and constitute an orifice through which a metered sample of biological fluid can be introduced by a syringe of the like into the shear region between the inner and outer bearing surfaces. Support assemblage 24 is in the form of horizontal rod 40, that, as shown, is adapted to be manually held. The outer diameter of rod 40 and the outer diameter of bearing ring 28 are the same so as to establish a continuous cylindrical surface. On rod 40 is a marker 42, which indicates the desired axial location of outer bearing assemblage 22 on inner bearing assemblage 20. Bias assemblage 26 includes a threaded shaft 44 that extends radially from annualar bearing mount 22 and a threaded nut 46 that is turned onto shaft 44 to an adjusted position at which selected bias is achieved.

In accordance with the present invention, each of the bearing surfaces requires a surface finish ranging from 8 to 125 microinches in average valley to peak height. Also, the spacing or tolerance between the bearing surfaces ranges from 0.01 to 10.0 mils and preferably from 1 to 5 mils. Preferably the axial thickness of outer bearing member 22 ranges from ¼ to 2 inches. Preferably each of the bearing members is composed of a dimensionally stable, sterilizable material, for example, a vitreous material such as glass, a metallic material such as stainless steel, or a plastic material such as methyl methacrylate.

The following non-limiting examples further illustrate the present invention. In each of these examples the axial length of outer ring 32 was approximately 2 centimeters, the radial distance between the inner and outer bearing surfaces was approximately 0.01 millimeter, and the bearing surfaces each had areas of approximately 500 millimeters. The process of the present invention contemplates indicating visco-elastic changes resulting from pathological conditions, drug usage, the menstrual cycle, etc.

EXAMPLE I

In the case of obstructive pulmonary diseases such as bronchitis, cystic fibrosis and emphysema, thick viscous discharges are expectorated. The obstructive fractions are intermixed with saliva, pulmonary surfactants, bacteria, water, electroytes and other components. There are no "pure samples" and no two consecutive specimens are alike since they may originate from the bronchi or alveoli in different locations in the lungs involving regions that may be more or less seriously involved. Certain drugs known as mucolytic agents are used to liquefy the tenacious viscous fractions although their efficacy is difficult to measure. In accordance with the present invention, testing a sample of such an expectorated discharge involves inserting it into the shear region between the two bearing surfaces of the test instrument and biasing the bearing surfaces for relative movement in order to determine the lubricity of the residue.

EXAMPLE II

The present invention is useful in determining the phase of the menstrual cycle and, particularly, to indicating the rheological properties of bodily mucus, particularly cervical mucus and/or oral mucus, in order to predict the inception and to indicate the presence of ovulation. The present invention thus is concerned with conception control. It has been found that mucus samples from the vaginal and oral cavities undergo distinct in-phase rheological changes during the menstrual cycle. Although the changes in the cervical mucus are much more noticeable than the changes in the oral mucus, both changes are readily determinable. During the immediate pre-ovulatory phase, for a period of one to three days under estrogen domination, the mucus is profuse and watery. During the post-ovulatory phase, under pregestation, the mucus becomes less abundant and more viscous. In healthy women with normal menstrual cycles, as is well documented in the medical literature, ovulation usually occurs between the 12th and 14th day prior to the next menstrual period (and not after the preceding period). Specifically, cervical mucus is most hydrated at the time of ovulation, containing 97 to 98% water, and is relatively dehydrated at other times, containing only 80 to 90% water. The solid residue after desiccation may range from 2% during ovulation to 20% at other times, a ten fold increase. In accordance with the present invention, testing a sample of cervical mucus involves inserting it into the shear region between the two bearing surfaces of the test instrument and biasing the bearing surfaces for relative motion in order to determine the lubricity of the residue.

In each of the foregoing examples, testing of the residue involved establishing a predetermined torque, which either causes rotation of the outer bearing member or does not cause rotation of the outer bearing member as an indication of lubricity. It is to be understood that the present invention contemplates a variety of control techniques by which precise measurements of lubricity value can be obtained. Since certain changes may be made in the present disclosure without departing from the scope hereof, it is intended that all matter contained in the above specification or shown in the accompanying drawing be interpreted in an illustrative and not in a limiting sense.

What is claimed is:

1. A device for testing mucus from a bodily cavity, said device comprising a base, inner bearing means and outer bearing means, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed in operation with respect to said base, said base including an elongated rod, said inner bearing member projecting from said rod and being substantially coaxial therewith, said rod including means for indicating the position of said outer bearing member with respect to said rod.

2. A device for testing mucus from a bodily cavity, said device comprising a base, inner bearing means and outer bearing means, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed in operation with respect to said base, said base including an elongated rod, said inner bearing member projecting from said rod and being substantially coaxial therewith, said outer bearing means including an aperture through which said mucus can be inserted into said clearance.

* * * * *